(12) United States Patent
McLeod et al.

(10) Patent No.: US 6,234,975 B1
(45) Date of Patent: May 22, 2001

(54) NON-INVASIVE METHOD OF PHYSIOLOGIC VIBRATION QUANTIFICATION

(75) Inventors: Kenneth J. McLeod, Stony Brook; Robert Huang; Clinton T. Rubin, both of Port Jefferson, all of NY (US)

(73) Assignee: Research Foundation of State University of New York, Stony Brook, NY (US)

( * ) Notice: Subject to any disclaimer, the term of this patent is extended or adjusted under 35 U.S.C. 154(b) by 0 days.

(21) Appl. No.: 09/498,962

(22) Filed: Feb. 4, 2000

Related U.S. Application Data

(63) Continuation of application No. PCT/US98/16539, filed on Aug. 5, 1998.
(60) Provisional application No. 60/054,721, filed on Aug. 5, 1997.

(51) Int. Cl.[7] .................................................... A61B 5/00
(52) U.S. Cl. ............................................ 600/552; 600/587
(58) Field of Search .................................... 600/552, 553, 600/587, 595; 606/46, 49

(56) References Cited

U.S. PATENT DOCUMENTS

| 4,175,546 | * | 11/1979 | Goldblatt et al. | 600/552 |
| 4,416,269 | * | 11/1983 | Enomoto et al. | 601/61 |
| 4,754,763 | * | 7/1988 | Doemland | 600/552 |
| 4,771,792 | * | 9/1988 | Seale | 600/587 |
| 5,273,028 | | 12/1993 | McLeod et al. | 601/35 |
| 5,368,044 | * | 11/1994 | Cain et al. | 600/552 |
| 5,402,781 | * | 4/1995 | Dimarogonas | 600/407 |
| 5,836,876 | * | 11/1998 | Dimarogonas | 600/407 |

FOREIGN PATENT DOCUMENTS

| 86/03393 | 6/1986 | (WO) . |
| 96/29930 | 10/1986 | (WO) . |
| 97/00643 | 1/1997 | (WO) . |

OTHER PUBLICATIONS

Maki et al., "A Posture Control Model and Balance Test for the Prediction of Relative Postural Stability", IEEE Transactions on Biomedical Engineering, vol. 34, No. 10, Oct. 1987, pp. 797–810.

Johansson et al., "Identification of Human Posture Dynamics", IEEE Transactions on Biomedical Engineering, vol. 35, No. 10, Oct. 1988, pp. 858–869.

(List continued on next page.)

*Primary Examiner*—Eric F. Winakur
*Assistant Examiner*—Charles Marmor, II
(74) *Attorney, Agent, or Firm*—Dilworth & Barrese

(57) ABSTRACT

The present disclosure describes a method of determining the onset of osteoporosis by measuring the vibrational response of the musculoskeletal system. Risk of fracture of bones due to osteoporosis is mainly determined by three risk factors: muscle strength, bone mass, and postural stability. Because these three risk factors for fractures are interrelated and dependent on muscle function, they can be determined by quantifying physiologic vibration non-invasively using a low-mass accelerometer placed at an appropriate muscle belly. Muscle vibrations are produced by force fluctuations of unfused motor units during contraction and are expressed by the lateral expansion of muscle fibers. Muscle vibrational characteristics span a broad (0–100 Hz) frequency regime, directly reflecting the force provided by the muscle fibers being utilized and the nature of the dynamic mechanical milieu experienced by the skeleton during postural or locomotory muscle activity. In addition vibrational information below 5 Hz has been shown to correspond to postural instability. Also, a specific frequency component of the muscle vibration spectrum (25–50 Hz) has now been shown to represent the contribution of fast-oxidative fibers which are well correlated to the bone mineral density of humans. Thus, all three of the major risk factors of fracture are measured by a simple measurement of the musculoskeletal vibration spectrum using physiologic vibration quantification.

21 Claims, 2 Drawing Sheets

OTHER PUBLICATIONS

Shim et al. "Modulation of Osteoblast Proliferation and Differentiation by Subtle Alterations in Temperature" $42^{nd}$ Annual Meeting, Orthopaedic Research Society, Feb. 19–22, 1996, Atlanta, Ga.

Pope et al., "Transmission of Whole Body Vibration in the 10–40 HZ Range into the Hip and Lumbar Spine," $42^{42}$. Annual Meeting, Orthopaedic Research Society, Feb. 19–22, 1996, Atlanta, Ga.

Rubin et al., "Site–Specific Increases in Bone Density Stimulated Non–Invasively by Extremely Low Magnitude Thirty Hertz mechanical Stimulation", $43^{rd}$ Annual Meeting, Orthopaedic Research Society, Feb. 9–13, 1997 San Francisco, Ca.

Qin et al. "Correlation of dilatational Strain Gradients to Fluid Flow and Streaming Potentials in an in Vivo Animal Model" $43^{rd}$ Annual Meeting, Orthopaedic Research Society, Feb. 9–13, 1997 San Francisco, Ca.

McLeod et al., "Improved Postural Stability Following Short Term Exposure to Low Level Whole Body Vibration," $44^{th}$ Annual Meeting, Orthopaedic Research Society, Mar. 16–19, 1998, New Orleans, La.

Qin et al. "The Interdependent Role of Loading Frequency, Intracortical Fluid Pressure and Pressure Gradients in Guiding Site–Specific Bone Adaptation," $44^{th}$. Annual Meeting, Orthopaedic Research Society, Mar. 16–19, 1998 New Orleans, La.

Qin et al. "The Influence of Intramedullary Hydrostatic Pressure on Transcortical Fluid Flow Patterns in Bone", $43^{rd}$ Annual Meeting, Orthopaedic Research Society, Feb. 9–13, 1997, San Francisco, Ca.

* cited by examiner

NON-INVASIVE METHOD OF PHYSIOLOGIC VIBRATION QUANTIFICATION

This is a continuation of copending application Ser. No. PCT/US98/16539 filed Aug. 5, 1998 which claims the benefit of U.S. Provisional Application No. 60/054,721 filed Aug. 5, 1997.

BACKGROUND

1. Technical Field

This disclosure relates to the diagnosis of bone loss, more particularly, to a method of diagnosing osteoporosis, osteopenia and sarcopenia at an early stage.

2. Description of the Related Art

Osteoporosis is a pernicious disorder usually, but not exclusively, afflicting elderly women. The osteoporotic state can also be manifest by those who are confined to bed and even to astronauts who are subjected to weightlessness. Osteoporosis occurs through a decrease in bone mass which makes the afflicted bones more fragile and more susceptible to breaking.

The fractures resulting from osteoporosis can cause death, require extended hospital stays and sometimes involve expensive and painful surgery. Health care costs in this area range in the billions of dollars per year in the United States alone. In addition, osteoporosis severely diminishes the mobility and vitality of those afflicted with the disease.

The reduction in bone mass from osteoporosis results when destruction outpaces bone formation. The balance between destruction and formation is affected by hormones, calcium intake, vitamin D and its metabolites, weight, smoking, alcohol consumption, exercise and many other factors.

Osteoporosis is not easily determined in its early phases as physical deformity is not yet evident. Because osteoporosis develops progressively, early diagnosis and appropriate treatment may help to delay, if not avoid a serious condition. Appropriate diet and exercise can be used in early years to prevent the damaging effects of osteoporosis later in life. Methods for maintaining or promoting bone growth are described in numerous patents. For example, McLeod and Rubin, U.S. Pat. Nos. 5,103,806, 5,191,880, 5,273,028 and 5,376,065 collectively describe non-pharmacological means and methods for promoting bone growth and preventing bone loss. The method described in the above referenced patents describes a mechanical vibrational loading of bones to promote growth in a non-invasive procedure. McLeod and Rubin, U.S. Pat. Nos. 5,103,806, 5,191,880, 5,273,028 and 5,376,065 are all incorporated herein by reference.

The existing technology for predicting fracture risk and osteoporosis exposes the patient to cumulative doses of X-rays. The invasive nature of X-ray radiation is compounded by multiple exposures whenever the patient is to be reevaluated. Typical X-ray scanners are very expensive and require extensively trained technicians to operate. Further, these methods report only bone density, and do not directly indicate bone strength or tendency for bone loss.

Another method of diagnosing osteoporosis is to estimate bone mass through ultrasound velocity measurements. Unfortunately, these tests are limited to bones, such as the calcaneus and patella, which do not suffer from osteoporosis and are only weakly indicative of risk of fracture. Traditional bone mass measurements, by their very nature, are unable to predict bone loss prior to its occurrence and can only chart the course of bone loss over an extended period of time. Further, these diagnostics only consider bone mass, and fail to consider other factors such as tendency to fall, or ability to protect yourself during falling.

Since it is desirable to institute treatment for osteoporosis early on, a need exists for an inexpensive, non-invasive technique for diagnosing osteoporosis in its early stages.

SUMMARY

The present disclosure describes a method of determining the onset of osteoporosis by measuring, non-invasively, the vibrational characteristics of the musculoskeletal system. These measurements can be taken during both voluntary and involuntary muscle stimulation. Risk of fracture of bones due to osteoporosis is mainly determined by three risk factors: muscle strength, bone mass and postural stability. Because these three risk factors for fractures are interrelated and dependant on muscle function, they can be determined by quantifying physiologic vibration non-invasively. This quantification can be done either with or without external stimulus to the patient. For example, all people sway during quiet standing, thereby stimulating muscle activity. Alternately, the patient may be subjected to perturbation to stimulate muscle activity. For example, under the influence of an upper body perturbation on a standing patient, a younger patient will typically exhibit a fluid "sway" away from and then back toward the source whereas, in an older patient, the response is more stiff and resistant. External stimulation can be accomplished by, e.g., using a vibration generating device such as, a shaker table.

Muscle vibrations are produced by the normal force fluctuations of unfused motor units during contraction and are expressed by the lateral expansion of muscle fibers during both quiet standing and/or gait. Musculoskeletal vibrational characteristics span a broad (0–100 Hz) frequency regime, directly reflecting the types of muscle fibers being utilized and the nature of the dynamic mechanical milieu experienced by the skeleton during postural or locomotory muscle activity. Muscle vibrational characteristics have been shown to be reflective of muscle mechanical activity correlating to muscle strength but they also are an important determinant of bone mass. While muscle vibrations less than 25 Hz correlate with muscle strength, we have shown that a specific frequency component of the muscle vibration spectrum (25–50 Hz) represents the contribution of fast-oxidative fibers which are well correlated to the bone mineral density of humans. In addition, we have shown that postural sway measurements can be simultaneously obtained with the muscle vibration measurement when using an accelerometer to obtain the latter. Thus, all three of the major risk factors of osteoporotic fracture are measured by a simple measurement of the musculoskeletal vibration spectrum using physiologic vibration quantification. This can be an important early marker for the tendency to develop osteoporosis and/or susceptibility to bone fracture with age.

A non-invasive method for evaluating musculoskeletal tissue includes the steps of connecting one or more vibration measurement devices to an external location(s) on a body. For locations over a muscle, the vibrational characteristics of the muscle and skeletal system can be obtained, given measurement over a predetermined period of time. A frequency decomposition or other time series analysis (fractal techniques, diffusion techniques, etc.) approach can be used to quantify the vibrational spectrum to evaluate muscle strength, postural stability and bone density.

In other methods, the step of determining bone mineral density by evaluating the vibrational response in a frequency range of between about 25 Hz and about 50 Hz may be included. The step of determining postural stability by evaluating the vibrational response in a frequency range of below about 5 Hz may also be included. The vibrational response may be measured concurrent with inducing vibrations within the muscle by an external stimulation device. The vibration measurement device may include a low-mass cantilever beam accelerometer. The step of analyzing the vibrational spectrum may further include the step of comparing the vibrational spectrum to vibrational spectrums of a same category. The same category may include individuals having at least one of age, sex and body type in common. The predetermined amount of time may be about 0.5 to about 5 minutes.

A non-invasive physiologic vibration quantification system for evaluating a musculoskeletal system may include vibration means for externally transferring vibrations or other displacements to the musculoskeletal system. A vibration measurement device is included for mounting externally to a body over a muscle, the vibration measurement device for measuring a response by the muscle in accordance with the vibrations/displacements transferred by the vibration means, the vibration measurement device for forming signals representative of the musculoskeletal response. An analyzer is coupled to the vibration measurement device for receiving the signals from the vibration measurement device and developing a time series data analysis (for example, spectrum analysis) associated with the signals, the analysis providing vibrational quantification of the musculoskeletal system for evaluating muscle strength, postural stability and bone density.

In alternate embodiments, the vibrating means may include a vibration table. The vibration table may generate frequencies between about 0 Hz and about 100 Hz and may generate peak amplitudes between about 0.04 g's and about 0.4 g's. The vibration measurement device may include a low mass cantilever beam accelerometer. A preamplifier may be included for amplifying the signals to the analyzer. A recording means may also be included for recording vibrational responses of the muscle.

These and other objects, features and advantages of the present invention will become apparent from the following detailed description of illustrative embodiments thereof, which is to be read in connection with the accompanying drawings.

BRIEF DESCRIPTION OF DRAWINGS

The invention will be described in detail in the following description of preferred embodiments with reference to the following figures wherein.

DETAILED DESCRIPTION OF PREFERRED EMBODIMENTS

Figure 1:
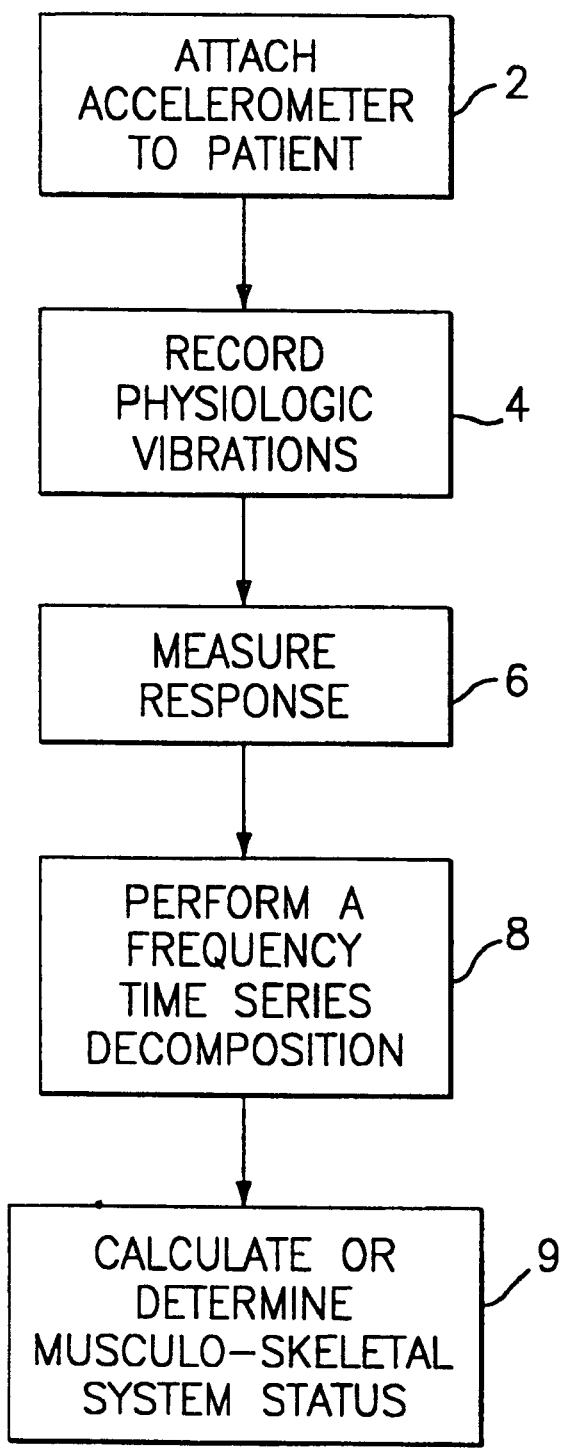
FIG. 1 is a flow diagram showing the steps for quantification of physiologic vibration.

The present disclosure describes an apparatus and method for determining the susceptibility to bone fracture and/or the onset of osteoporosis by measuring the vibrational response of a musculoskeletal system. Risk of fracture of bones due to osteoporosis is mainly determined by three risk factors: muscle strength, bone mass and postural stability. Because these three risk factors for fractures are interrelated and dependant on muscle function, they can be determined by quantifying physiologic vibration non-invasively using a low mass cantilever beam accelerometer placed over an appropriate musculoskeletal site.

Low-mass cantilever beam accelerometers typically employ a cantilever with one end supported on a mount and a proof mass on the other. Such a beam is typically micromachined from silicon, and one or more strain gauges are disposed on its surface at a desired sensing site. These one or more strain gauges are connected in an electric circuit to provide a signal indicative of acceleration-induced strain in the beam. The proof mass used is low in order to allow measurements at higher frequencies, since the natural frequency of the beam varies as the inverse square root of the mass. Low mass cantilever beam strain gauge accelerometers are desirable because of their high sensitivity and their frequency response which extends down to D.C. See, e.g. U.S. Pat. No. 5,412,987 to Bergstrom et al. which is incorporated herein by reference. Alternatively, low cost solid state, variable capacitance accelerometers may be used, which, while less sensitive, are more robust.

Muscle vibrations in both voluntary and involuntary muscles are produced by force fluctuations of unfused motor units during contraction and are expressed by the lateral expansion of muscle fibers. Muscle vibrational characteristics span a broad (0–100 Hz) frequency regime, directly reflecting the types of muscle fibers being utilized and the nature of the dynamic mechanical milieu experienced by the skeleton during postural or locomotory muscle activity. This muscular activity is stimulated for example by simply having the patient stand quietly, as the patient will naturally rock or sway during quantification. Alternately, the patient can be subjected to some form of perturbation.

Muscle vibrational characteristics have been shown to be reflective of muscle mechanical activity correlating to muscle strength but they also are an important determinant of bone mass. While muscle vibrations less than 25 Hz correlate with muscle strength, we have shown that a specific frequency component of the muscle vibration spectrum (about 25–50 Hz) represents the contribution of fast-oxidative fibers which are well correlated to the bone mineral density of humans independent of age ($r=0.58$, $p<0.02$ where r represents the correlation coefficient and p represents the probability that the relationship is not fortuitous). Furthermore, this same frequency component (about 25–50 Hz) of muscle contraction dynamics decreases in intensity as a function of age ($r=-0.62$, $p=0.001$). Thus, loss of the high frequency dynamics of muscle contraction (i.e., loss of fast-oxidative muscle fibers) is similar to that for age-related osteoporosis (approximately 1.5% per year).

An appropriately mounted low mass accelerometer can be used to measure vibrational characteristics down to 0 Hz allowing the quantification of postural sway in the very low frequency vibration spectrum. When postural sway is measured as very low frequency vibrations (about 0–5 Hz), the vibration spectrum indicates an increasing amount of sway and postural instability as a function of age ($r=0.49$, $p=0.0014$). This is consistent with the current understanding of posture. Thus, all three of the major risk factors of fracture in the elderly are measured by a simple measurement of the musculoskeletal vibration spectrum using physiologic vibration quantification. To summarize, postural sway is measured in the range of about 0–5 Hz, muscle strength in the range of about 5–25 Hz and bone density in the range of about 25–50 Hz.

The ability to characterize normal and abnormal physiologic vibrations in the musculoskeletal system has applications outside prediction of fracture risk. For example, the efficacy of antispasmatic drugs, such as those used to treat Parkinson's disease, could be objectively evaluated by physiologic vibration quantification. In addition, efficacy of physical therapy, physical training or exercise regimen, could be evaluated with these techniques. Directly related to physical therapy, the classification of when normal function has returned may be utilized to identify, and prevent, malingering.

Analysis of physiologic vibration may also be utilized in real time applications by incorporating these objective measures as feedback within prosthetic or other robotic control systems to assist in locomotion or to prevent falling, or other inappropriate or hazardous movement. Similarly, physiologic vibration measurements can be utilized in training modality whereby an acoustic or visual feedback to the patient/subject could provide a cue by which an individual could practice/exercise specific muscle groups or musculoskeletal action (e.g., in certain athletic events). Finally, physiologic vibration quantification can be used for the control of muscle force output in virtual environments (e.g., remote manipulation of hazardous substances, ground based control in space or deep sea environments).

In addition, other applications for physiologic vibration quantification may prove to be just as important as prediction of osteoporosis and fracture. These may include assessment of muscle fatigue, diagnosis of neuromuscular disorders, evaluation of adequacy and appropriateness of exercise regimes in terms of optimal muscle function, and tracking progress of physical therapy, physical training, or exercise regimen. Physiologic vibration quantification can also be used to evaluate gait and postural abnormalities which may determine when a person is sufficiently stable to operate heavy machinery or motor vehicles.

Ultimately, the assessment of risk for osteoporosis and subsequent bone fracture using physiologic vibration quantification provides a better prediction of fracture risk than a simple measure of bone mass. When etiologic factors are taken into account in determining fracture risk, physiologic vibration quantification will provide an early indicator for osteoporosis and allow preventive measures to be instituted prior to the onset of symptomatic bone loss.

The assessment of osteoporosis and fracture risk via muscle vibrational characteristics has a number of features and advantages over traditional bone mass determination. First, muscle vibrational assessment is an entirely non-invasive diagnostic procedure. The existing technology for predicting fracture risk and osteoporosis exposes the patient to cumulative doses of X-ray. Second, the muscle vibration assessment device is far less expensive to construct and maintain, and more convenient to utilize than traditional bone mass determination. Use of this device is as easy to use as an ECG monitor, and therefore, may be used in a primary care physician's office. Third, muscle vibration assessment detects the mechanical signals that are required for bone maintenance so that a diagnosis of sacropenia with a presumptive diagnosis of osteopenia can be made prior to symptomatic bone loss.

Traditional bone mass measurements, by their very nature, are unable to predict bone loss prior to its occurrence and can only chart the course of bone loss over an extended period of time. Muscle vibration assessment has the potential to determine which patients are at risk for bone loss and fracture on a mechanistic and etiologic basis prior to the development of bone loss. Finally, muscle vibration assessment appears to be better suited to predict fracture risk than traditional bone mass measurement because the major risk factors for fractures in the elderly (muscle strength, the primary stimulus for the creation/maintenance of bone mass, and postural sway) can simultaneously be determined. The early detection of patients at risk for osteoporosis will allow earlier intervention and therefore more effective prevention. In the era of cost-savings and preventive medicine, muscle vibration assessment could provide an effective screening tool for identifying patients who are at risk of developing osteopenia, osteoporosis, and ultimately, fractures.

Recent advances in the relationship between skeletal muscle activity and bone structural integrity have confirmed the potential for a diagnostic tool based on detecting deficiencies in muscle activity, and thereby, people predisposed to developing osteoporosis. Low amplitude mechanical stimuli applied to turkey, sheep, and human models of osteopenia have been shown to be capable of significantly influencing bone adaptation when the stimuli is applied in a frequency range of 20–60 Hz. Using physiologic vibration quantification, it can be shown that muscle dynamics within this frequency range correlates strongly with an individual's bone mineral density. In addition, these muscle vibrations decrease with age at a rate similar to the age-related decline observed for bone mass. These data strongly support the contention that skeletal muscle dynamics provide the necessary mechanical stimuli for maintaining the structural integrity of bone and that loss of a specific component of muscle vibration will result in decreased bone mass and integrity. Loss of muscle dynamics may prove to be the primary etiology for age related osteopenia. Furthermore, physiologic vibration quantification provides the ability to assess muscle strength and postural stability in conjunction with bone mass prediction, permitting a more accurate prediction of fracture risk than bone mass measurement alone. Thus, the non-invasive assessment of physiologic vibration allows for the early diagnosis of osteopenia and better prediction of risk of fracture for less cost than any competing technology, permitting preventive measures to be instituted prior to the onset of significant and symptomatic bone loss.

Referring now in specific detail to the drawings in which like reference numerals identify similar or identical elements throughout the several views, and initially to FIG. 1, a flow diagram of the vibrational quantification process is shown. In step 2, an accelerometer is attached to a patient on a predetermined muscle. In step 4, signals are generated within the muscle to create a measurable response from the musculoskeletal system. External vibrations and/or perturbation may be employed to create a measurable musculoskeletal response. This is particularly true for voluntary muscles which may have to be flexed to stimulate them. Involuntary muscles, such as postural muscles, typically do not require external stimulation instead measurable signals can be produced without external vibration or perturbation. Step 6 represents measuring/recording the muscle response by, for example, recording musculoskeletal vibrations as indicated by the accelerometer. Thereafter, in step 8, a frequency decomposition or other time series analysis/comparison is made to determine musculoskeletal status usin analyzer means. Also, response data is compared to previously collected spectral response data. Previously collected spectral data includes data obtained for individuals with similar characteristics to the patient, for example age, sex, body measurements, etc. Further, postural sway, muscle strength and bone density may be quantified and compared. Step 9 determines if a patient is susceptible to osteoporosis and/or bone fracture based on vibrational quantification.

Figure 2:
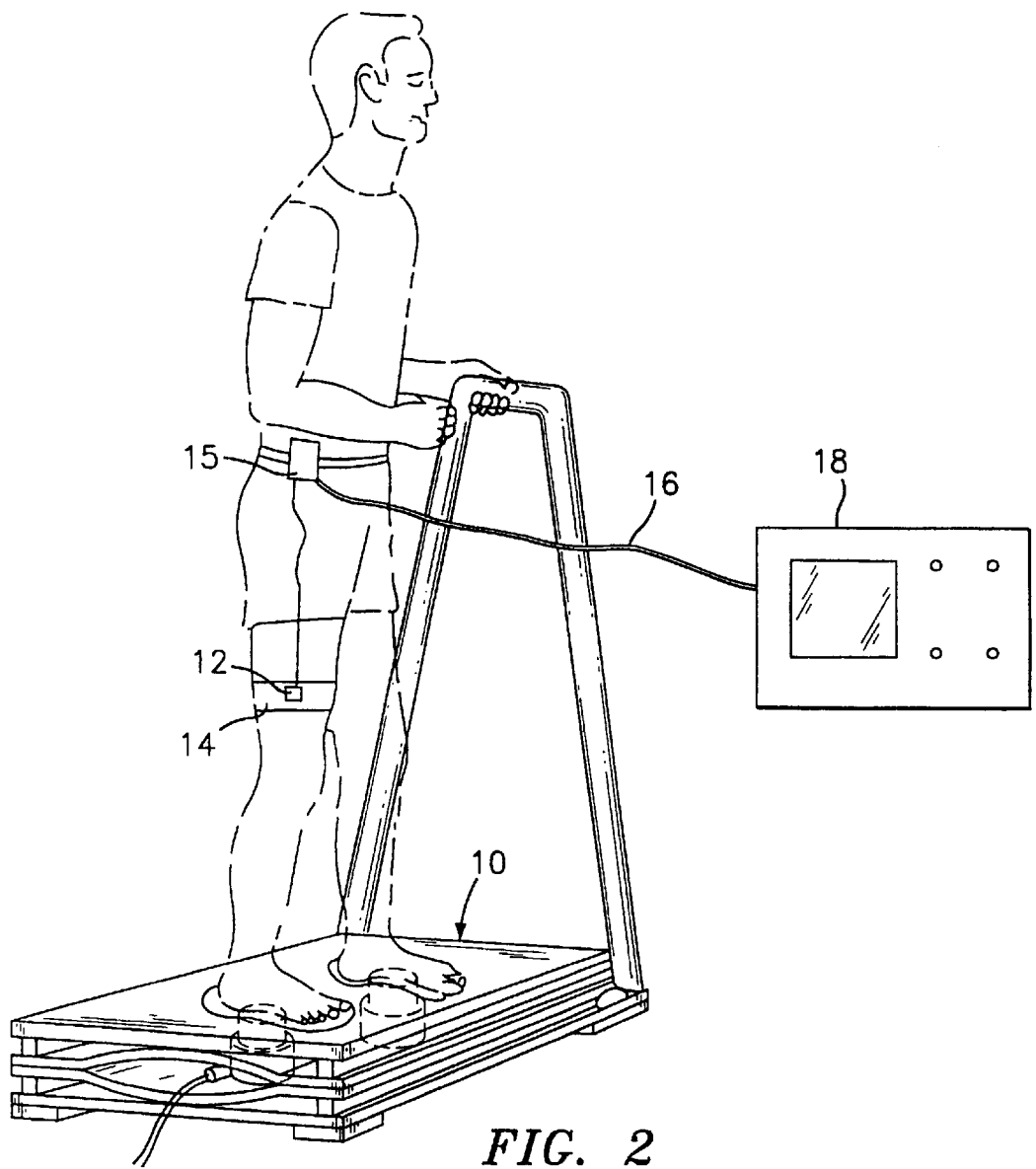
FIG. 2 is an isometric view showing an alternate embodiment of a vibration table with a patient undergoing vibrational quantification.

FIG. 2 shows a vibration quantification apparatus for an alternate embodiment. A patient stands on a vibration table 10. Vibrations, generated by the table for a predetermined duration, for example, 0.5–5 minutes, are transmitted through the patients body. The frequencies imparted by the table 10 are in the range between 0 and 100 Hz with a peak amplitude between 0.04 and 0.4 g's. The vibration waves are preferably sinusoidal, however other waveforms are contemplated. At least one low mass accelerometer 12 is used to measure the vibrational response of the muscle tissue in question. Accelerometer 12 is secured by straps 14 over the muscle belly of a muscle adjacent to a large bone, for example, the femur. During the vibration generation of table 10 the response of accelerometer 12 is amplified by preamplifier 15, typically worn on the patient. Thereafter, the response is measured and recorded by spectrum analyzer/computer 18 which is electrically connected to accelerometer 12 by a cable 16. The accelerometer response data is analyzed to extract information on postural sway, muscle strength and the muscle to bone stimulus. Data in the vibration spectrum of 25–50 Hz represents the contribution of fast-oxidative fibers and is of particular importance in correlating muscle dynamics with an individual's bone mineral density. Based on these three parameters a determination is made regarding the status of osteoporosis in the patient.

Having described preferred embodiments of a novel method of physiologic vibration quantification for diagnosing osteoporosis and postural stability (which are intended to be illustrative and not limiting), it is noted that modifications and variations can be made by persons skilled in the art in light of the above teachings. It is therefore to be understood that changes may be made in the particular embodiments of the invention disclosed which are within the scope and spirit of the invention as outlined by the appended claims. Having thus described the invention with the details and particularity required by the patent laws, what is claimed and desired protected by Letters Patent is set forth in the appended claims.

What is claimed is:

1. A non-invasive method for evaluating a musculoskeletal system comprising the steps of:
    connecting a vibration measurement device to an external location on a body, the location being over a muscle;
    measuring a vibrational response of the musculoskeletal system at the location;
    performing a frequency decomposition of the vibrational response to quantify the vibrational response into specific vibrational spectra; and
    analyzing the vibrational spectra to evaluate muscle strength, postural stability and bone density.

2. The method as recited in claim 1, further comprises the step of determining bone mineral density by evaluating the vibrational response in a frequency range of between about 25 Hz and about 50 Hz.

3. The method as recited in claim 1, further comprises the step of determining postural stability by evaluating the vibrational response in a frequency range of below about 5 Hz.

4. The method as recited in claim 1, further comprises the step of determining muscle strength by evaluating the vibrational response in a frequency range of between about 5 Hz and about 25 Hz.

5. The method as recited in claim 1, further comprising the step of inducing vibrations within the muscle by an external stimulation device.

6. The method as recited in claim 1, wherein the a vibration measurement device includes a low-mass accelerometer.

7. The method as recited in claim 1, wherein the step of analyzing the vibrational spectra includes the step of comparing the vibrational spectra to vibrational spectra of a same category.

8. The method as recited in claim 7, wherein the category includes at least one of age, sex and body measurement.

9. The method as recited in claim 1, wherein the step of measuring includes measuring the vibrational response of the muscle for a predetermined amount of time.

10. The method as recited in claim 9, wherein the predetermined amount of time is between about 0.5 minutes to about 5 minutes.

11. A non-invasive physiologic vibration quantification system for evaluating a musculoskeletal system comprising:
    vibration means for externally transferring vibrations to a musculoskeletal system;
    a vibration measurement device adapted for mounting to a body over a muscle, the vibration measurement device for measuring a response by the musculoskeletal system in accordance with the vibrations transferred by the vibration means, the vibration measurement device for forming signals representative of the musculoskeletal response; and
    analyzer means coupled to the vibration measurement device for receiving the signals from the vibration measurement device and developing a frequency spectrum associated with the signals, the frequency spectrum providing vibrational quantification of the musculoskeletal system for evaluating muscle strength, postural stability and bone density.

12. The system as recited in claim 11, wherein the vibrating means includes a vibration table.

13. The system as recited in claim 12, wherein the vibration table generates frequencies between about 0 Hz and about 100 Hz.

14. The system as recited in claim 12, wherein the vibration table generates peak amplitudes between about 0.04 g's and about 0.4 g's.

15. The system as recited in claim 11, wherein the vibration measurement device includes a low mass accelerometer.

16. The system as recited in claim 11, further comprises a preamplifier for amplifying the signals to the analyzer.

17. The system as recited in claim 11, wherein the vibration measurement device includes a solid state accelerometer.

18. The system as recited in claim 11, further comprises a recording means for recording vibrational responses of the muscle.

19. The system as recited in claim 11, wherein the frequency spectrum includes a response in a frequency range of between about 25 Hz and about 50 Hz for determining bone mineral density.

20. The system as recited in claim 11, wherein the frequency spectrum includes a response in a frequency range of below about 5 Hz for determining postural stability.

21. The system as recited in claim 11, wherein the frequency spectrum includes a response in a frequency range of about 5 Hz and about 25 Hz for determining muscle strength.

* * * * *